United States Patent
Kimata et al.

(10) Patent No.: US 6,866,517 B2
(45) Date of Patent: Mar. 15, 2005

(54) CONTACT SLIDABLE STRUCTURE WITH A HIGH DURABILITY

(75) Inventors: Takehito Kimata, Kariya (JP); Yasuyuki Sato, Kasugai (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/791,788

(22) Filed: Mar. 4, 2004

(65) Prior Publication Data

US 2004/0175992 A1 Sep. 9, 2004

(30) Foreign Application Priority Data

Mar. 4, 2003 (JP) .................................. 2003-057619

(51) Int. Cl.[7] ............................................ H01R 41/00
(52) U.S. Cl. ...................................... 439/33; 73/23.31
(58) Field of Search ........................... 73/23–31, 23.32, 73/31.05; 204/424, 426; 439/32, 33

(56) References Cited

U.S. PATENT DOCUMENTS

| | | | | |
|---|---|---|---|---|
| 4,983,271 A | * | 1/1991 | Kato et al. ................. | 204/426 |
| 5,246,562 A | * | 9/1993 | Weyl et al. ................. | 204/424 |
| 5,329,806 A | * | 7/1994 | McClanahan et al. ...... | 73/31.05 |
| 5,467,636 A | * | 11/1995 | Thompson et al. ......... | 73/23.31 |
| 5,490,412 A | * | 2/1996 | Duce et al. ................ | 73/23.31 |
| 5,546,787 A | * | 8/1996 | Hafele et al. .............. | 73/23.31 |
| 5,602,325 A | * | 2/1997 | McClanahan et al. ...... | 73/23.31 |
| 5,711,863 A | * | 1/1998 | Henkelmann et al. ...... | 204/428 |
| 5,739,414 A | * | 4/1998 | Paulus et al. .............. | 73/23.31 |
| 5,817,920 A | * | 10/1998 | Kuisell et al. ............. | 73/23.31 |
| 5,886,248 A | * | 3/1999 | Paulus et al. .............. | 73/23.31 |
| 5,922,938 A | * | 7/1999 | Hafele ...................... | 73/23.32 |
| 5,955,656 A | * | 9/1999 | Graser et al. .............. | 73/23.31 |
| 6,082,175 A | * | 7/2000 | Yoshikawa et al. ........ | 73/23.31 |
| 6,231,348 B1 | * | 5/2001 | Mayer et al. ............... | 439/33 |
| 6,266,997 B1 | * | 7/2001 | Nelson ...................... | 73/31.05 |
| 6,311,543 B1 | * | 11/2001 | Yoshikawa et al. ......... | 73/23.2 |
| 6,447,887 B1 | | 9/2002 | Claus et al. | |
| 6,453,726 B1 | * | 9/2002 | Gutierrez et al. .......... | 73/31.05 |
| 6,463,788 B2 | * | 10/2002 | Nakano et al. ............ | 73/31.05 |
| 6,477,887 B1 | * | 11/2002 | Ozawa et al. ............. | 73/31.05 |
| 6,613,206 B1 | * | 9/2003 | Weyl et al. ................ | 204/424 |
| 6,615,641 B2 | * | 9/2003 | Kojima ..................... | 73/23.31 |
| 6,637,256 B2 | * | 10/2003 | Shirai ....................... | 73/31.05 |
| 6,658,916 B2 | * | 12/2003 | Donelon et al. ........... | 73/23.31 |
| 6,672,136 B2 | * | 1/2004 | Kojima ..................... | 73/31.05 |
| 6,688,157 B2 | * | 2/2004 | Yamada et al. ............ | 73/23.2 |
| 6,719,950 B2 | * | 4/2004 | Day et al. .................. | 422/98 |
| 6,812,710 B2 | * | 11/2004 | Weyl et al. ................ | 324/464 |
| 2004/0074284 A1 | * | 4/2004 | Day et al. .................. | 73/23.31 |

FOREIGN PATENT DOCUMENTS

| | | |
|---|---|---|
| JP | 2001-188060 | 7/2001 |
| JP | 2002-286681 | 10/2002 |

* cited by examiner

*Primary Examiner*—Ross Gushi
(74) *Attorney, Agent, or Firm*—Nixon & Vanderhye P.C.

(57) ABSTRACT

A contact slidable structure is formed between a resilient terminal and a terminal electrode. The terminal electrodes and are disposed on the ceramic element. The resilient terminals and are resiliently deformed and forced to press the terminal electrodes and. The ceramic element has the ceramic body, inner leads and formed inside the ceramic body, terminal electrodes and disposed on the outer surfaces and, and conductive through holes and electrically connecting the inner leads and with the terminal electrodes and, respectively. In the ceramic element, the resilient terminals and are placed slidably on the outer surfaces and of the terminal electrodes and to form the contact slidable structure, and the conductive through holes and are not formed within the contact slidable areas and to the terminal electrodes and, respectively.

19 Claims, 13 Drawing Sheets

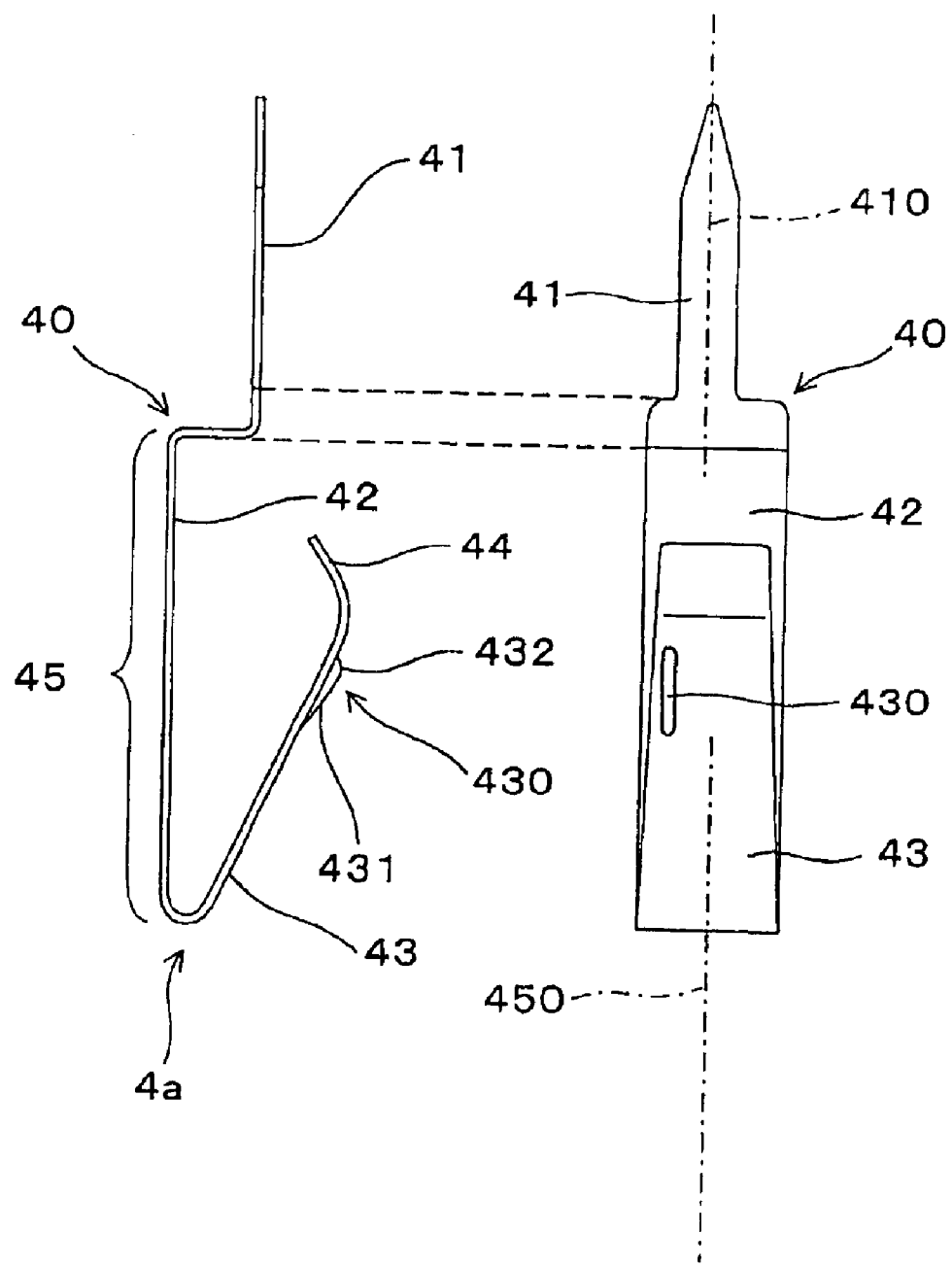

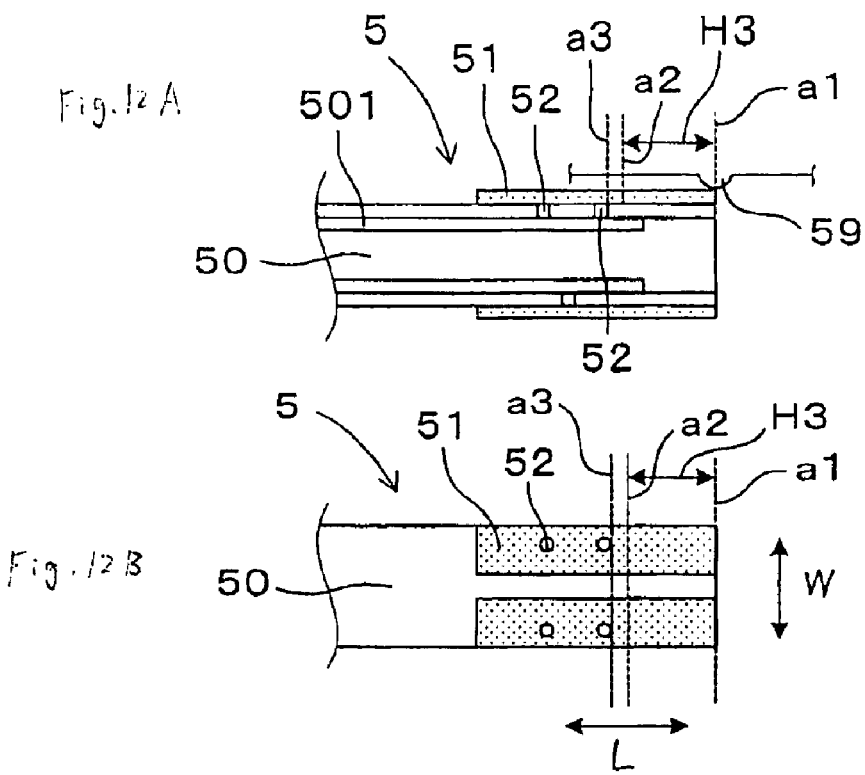
Fig. 12A
Fig. 12B
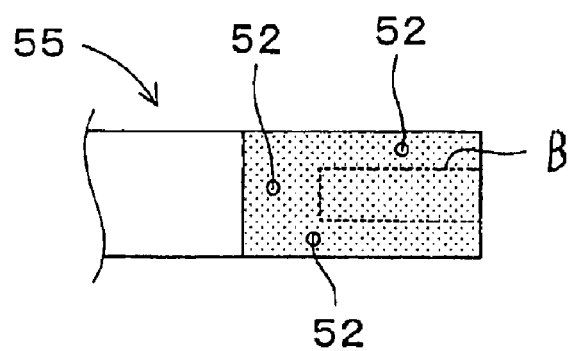
Fig. 13

CONTACT SLIDABLE STRUCTURE WITH A HIGH DURABILITY

BACKGROUND OF THE INVENTION

1. Technical Field of the Invention

The present invention relates generally to a contact slidable structure formed by a resilient terminal and a terminal electrode of a ceramic element such as a gas sensing element used in a gas sensor capable of measuring concentration of a predetermined component contained in an automotive exhaust gas.

2. Background Art

In an exhaust gas system of an automotive internal combustion engine, a gas sensor for measuring concentration of a predetermined component, such as oxygen gas, NOx and others, is installed to control combustion in the engine and to detect deterioration in a catalyst installed in the automotive exhaust gas system.

Japanese Patent Application Laid-open No.2002-286681 and U.S. Pat. No. 6,447,887 (Japanese Patent Application Laid-open No.2001-188060) disclose conventional gas sensing element.

As a type of the gas sensing element being installed in the gas sensor, a build-up gas sensing element having the structure as shown in FIGS. 5 and 6 mentioned later is known.

As shown in FIG. 6 mentioned later, the above gas sensing element has a ceramic body, an inner lead built in the ceramic body, a terminal electrode formed on an upper surface of the ceramic body, and a conductive through hole extending between the inner lead and the terminal electrode to form an electrical connection between the inner lead and the terminal electrode.

Furthermore, in order to feed electric power to the gas sensing element or pick up an output from the element, a resilient terminal made of a resilient metal is used for being in contact with the terminal electrode of the gas sensing element, as shown in FIG. 1 referred to later and in FIGS. 3,11,12 and 16 of U.S. Pat. No. 6,447,887.

However, heretofore, the following problems are known to arise in case of using the resilient terminal having the above structure.

More specifically, strength of the terminal electrode is deteriorated at the portion thereof where the conductive through hole is formed. Thus, cracks running from an edge of the thorough hole to the ceramic body may be generated, due to restoring force of the pre-stressed resilient terminal when the resilient terminal slides over the conductive through hole.

As shown in FIG. 16, the resilient terminal 99 slides leftwards in FIG. 16 while being in contact with the ceramic element 9 having the ceramic body 90, the inner lead 91, the terminal electrode 92 and the though hole 93 formed between the inner lead 91 and the terminal electrode 92, to form a contact slidable structure between the inner lead 91 and the terminal electrode 92. The restoring force of the resilient terminal 99 applied to the ceramic element 9 when the resilient terminal 99 slides over the ceramic element 9 while being in contact with the ceramic element 9 causes the crack 901 running from an edge of the conductive through hole 93 to the ceramic body 90.

Furthermore, as shown in FIG. 17, the insulating layer 95 may be formed onto the back surface of the inner lead 91 of the ceramic element 9. In case that the opening 930 penetrating into the conductive through hole 93 is formed by a pressure applied from the resilient terminal sliding over the conductive through hole 93, the ingredients contained in the insulating layer 95 formed under the conductive through hole 93 may exude through the opening 930 formed in the conductive through hole 93 over the upper surface of the terminal electrode 92 to form the insulating coating 931, which may cause conductive deterioration between the resilient terminal 99 and the terminal electrode 92. The present invention is produced in view of the above problems of the background arts.

SUMMARY OF THE INVENTION

It is an object of the invention to provide a contact slidable structure to be formed between the ceramic element and the resilient terminal, which can settle the above problems in the background arts.

It is another object of the invention to provide a contact slidable structure with a high electrical conductivity and high durability.

The first aspect of the invention provides a contact slidable structure comprising: an element having a body, an inner lead formed in the body, a terminal electrode formed on an outer surface of the body, and a conductive through hole penetrating the body between the inner lead and the terminal electrode to form an electrical connection therebetween; and a resilient terminal slidably placed on an outer surface of the terminal electrode to form a contact with the terminal electrode, wherein the conductive through hole is formed outside a contact slidable area on which the contact slides when the element is connected to the resilient terminal.

According to the first aspect of the invention, no conductive through holes are present within an area where the resilient terminal may come into contact with the terminal electrode to form a contact slidable structure between the resilient terminal and the terminal electrode, thus, the conductive through holes are not subjected to a pressure applied from the resilient terminal to the terminal electrode when the resilient terminal slides on the terminal electrode while being in contact with the terminal electrode. Therefore, both an occurrence of cracks running from an edge of the conductive through hole to the ceramic body, due to a pressure applied from the resilient terminal to the terminal electrode, and a formation of an insulating coating on an outer surface of the terminal electrode, due to an insulating material exuded from an insulating layer is prohibited.

As described above, according to the first aspect of the invention, a contact slidable structure formed between the element and the resilient terminal, with a high electrical conductivity can be provided.

The first modification of the invention is based on the first aspect thereof, and provides a contact slidable structure wherein the conductive through hole is apart by at least 0.5 mm from the contact slidable area.

The second modification of the invention is based on the first aspect thereof, and provides a contact slidable structure wherein the resilient terminal is forced to press the terminal electrode to form the contact.

The third modification of the invention is based on the first aspect thereof, and provides a contact slidable structure as set forth in claim 3, wherein an end t2 of the terminal electrode is apart by at least 0.2 mm from an end t1 of the element.

The fourth modification of the invention is based on the fourth aspect thereof, and provides a contact slidable structure as set forth in claim 4, wherein the terminal electrode has a thickness of 3–50 μm at the end t2.

The fifth modification of the invention is based on the first aspect thereof, and provides a contact slidable structure as set forth in claim 1, wherein the element is a gas sensing element having an electrochemical cell for measuring concentration of a predetermined component contained in a measurement gas.

The second aspect of the invention provides an electrically connecting mechanism comprising: a first holder designed to hold an element which has a body and an electric circuit, the electric circuit including a first terminal formed on an outer surface of the body, an inner conductor disposed within the body, and a conductive through hole extending through the body to establish an electrical connection between the first terminal and the inner conductor; and a second holder which holds a second terminal, said second holder designed to establish a mechanical joint to said first holder and allow the element to slide on the second terminal and make an electrical contact of the first terminal with the second terminal upon establishment of the mechanical joint to said first holder, the second terminal being elastically deformable to apply a physical pressure to the first terminal of the element through the electrical contact, orientation of the physical pressure being out of alignment with the conductive through hole of the element.

The sixth modification of the invention is based on the second aspect thereof, and provides an electrically connecting mechanism wherein the second holder has a hole in which the element is accommodated.

The seventh modification of the invention is based on the second aspect thereof, and provides an electrically connecting mechanism wherein the conductive conductive through hole is out of alignment with respect to an area where the physical pressure acts upon establishment of the mechanical joint.

The eighth modification of the invention is based on the second aspect thereof, and provides an electrically connecting mechanism wherein the second terminal has a shape deformable in a direction departing from the upper surface of the element, along a normal line thereof.

The ninth modification of the invention is based on the second aspect thereof, and provides an electrically connecting mechanism wherein the second terminal is made up of a pair of terminal elements provided in the hole so that the element is clipped between the pair of terminal elements.

The third aspect of the invention provides A gas sensor comprising: a sensing element having a length and an electrical circuit sensing density of a predetermined component contained a measurement gas, a first holder holding a first end and a portion of a side of the sensing element while exserting a second end and a portion of a side of the sensing element, a second holder having a cavity accommodating the second end and the portion of the side of the sensing element, an inner lead embedded in the sensing element, electrically connected to the electrical circuit, an outer lead disposed on an outer surface of the sensing element, a conductive through hole formed at the sensing element, electrically connecting the inner lead with the outer lead, a resilient terminal affixed to an inner wall of the cavity, slidably placed on the outer lead, a lead assembled in the second holder, electrically connected to the resilient terminal, wherein the conductive through hole is formed outside an area on which pressure from the resilient terminal acts.

The tenth modification of the invention is based on the third aspect thereof, and provides a gas sensor as set forth in claim 12, wherein the sensing element has an embedded atmospheric chamber admitting air thereinto and a solid electrolytic substrate exposed to the atmospheric chamber, admitting the predetermined component thereinto, a solid electrolytic substrate exposed to the atmospheric chamber and a diffusion resistant layer laminated on the solid electrolytic substrate, admitting the predetermined component thereinto, and wherein the electrical circuit comprises a reference electrode affixed to a surface of the solid electrolytic substrate, exposed to the atmospheric chamber and a measurement gas side electrode affixed to the opposite surface of the solid electrolytic substrate.

The eleventh modification of the invention is based on the third aspect thereof, and provides a gas sensor wherein the conductive through hole is provided inside the area in a longitudinal direction of the sensing element.

The twelfth modification of the invention is based on the third aspect thereof, and provides a gas sensor wherein the conductive through hole is provided outside the area in a lateral direction of the sensing element.

The thirteenth modification of the invention is based on the third aspect thereof, and provides a gas sensor wherein an end of the terminal electrode is provided inside the second end of the sensing element in a longitudinal direction of the sensing element.

The fourteenth modification of the invention is based on the third aspect thereof, and provides a gas sensor as set forth in claim 12, wherein a thickness of the terminal electrode is 3–50 μm.

The fifteenth modification of the invention is based on the thirteenth aspect thereof, and provides a gas sensor wherein the terminal electrode is made up of a broader part locating on an outer surface of the ceramic element in the vicinity of the first end thereof and a narrower part extending toward the second end of the ceramic element.

The sixteenth modification of the invention is based on the thirteenth aspect thereof, and provides a gas sensor wherein the conductive through hole is provided on the narrower part.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

Figure 7A:
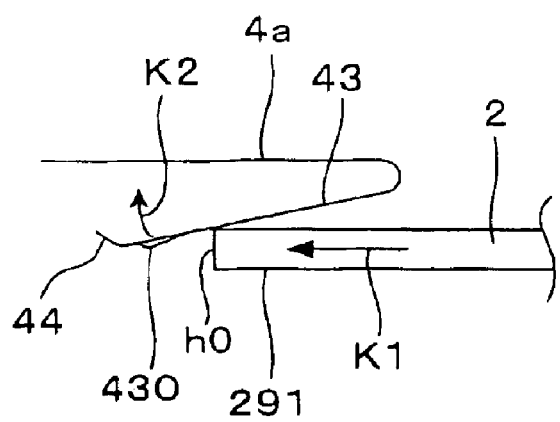
Figure 7B:
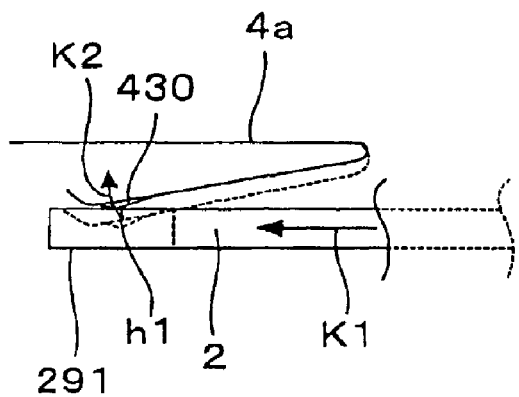

Each of FIGS. 7A and 7B is a schematic illustration showing a motion of a ceramic element when a resilient terminal slides on the ceramic element while being in contact with the ceramic element according to the first embodiment.

Figure 8:
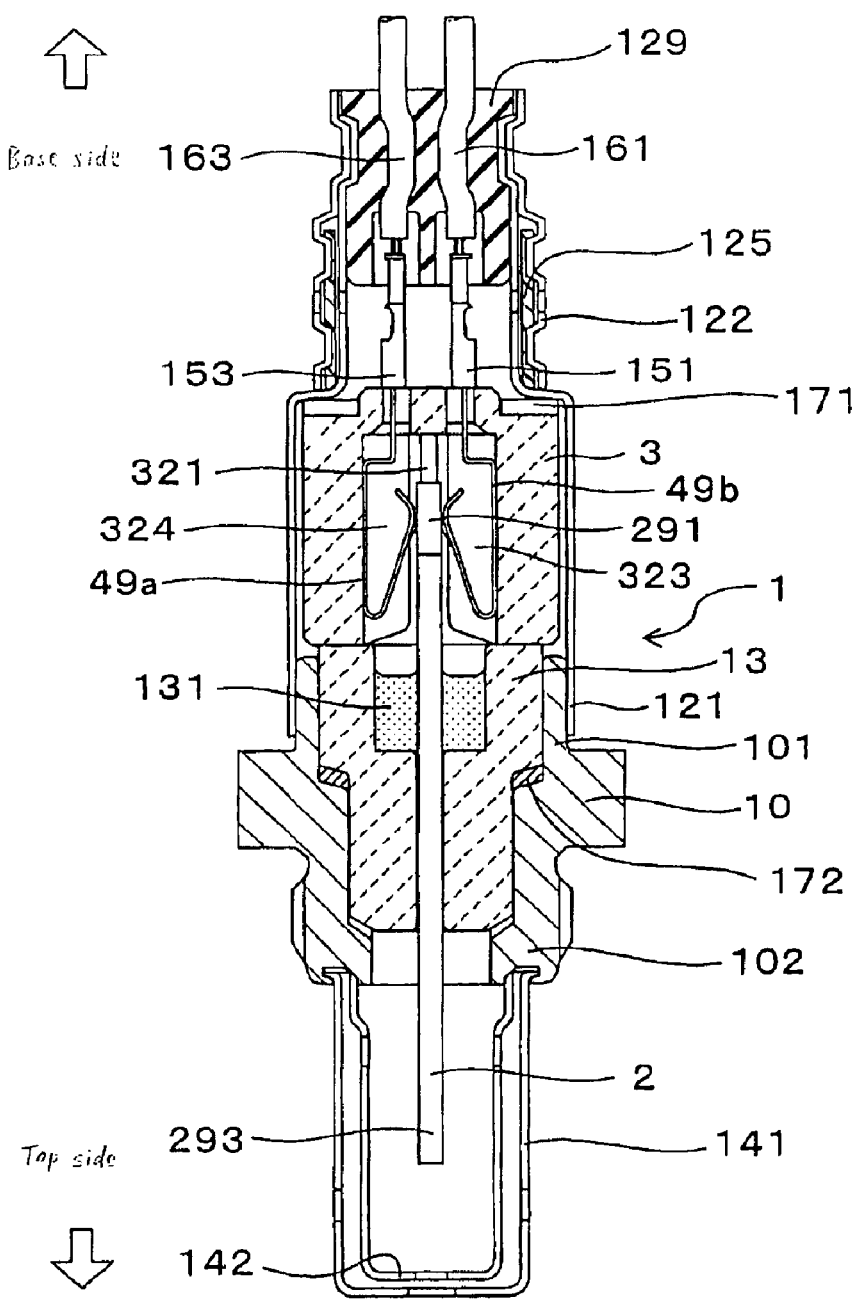

FIG. 8 is a cross-sectional view showing a gas sensor according to the first embodiment.

Figure 9A:
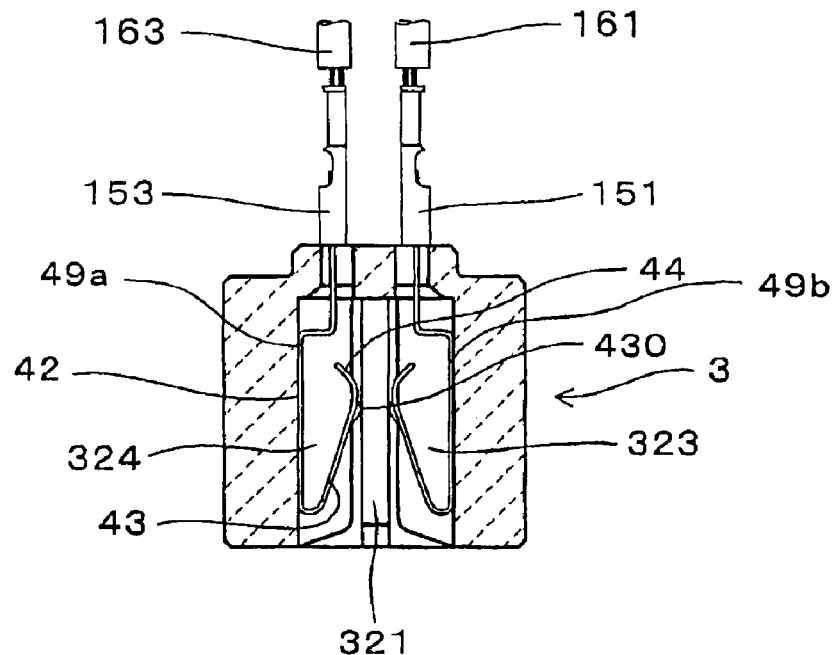

FIG. 9A is a cross-sectional view in a longitudinal direction of a gas sensor showing a resilient terminal accommodated in an insulator of a gas sensor according to the first embodiment.

Figure 9B:
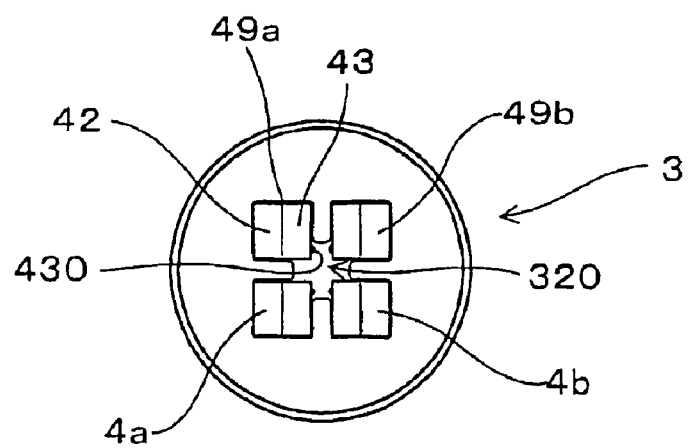

FIG. 9B is a cross-sectional view in a radial direction of a gas sensor showing a resilient terminal accommodated in an insulator of a gas sensor according to the first embodiment.

Figure 10:
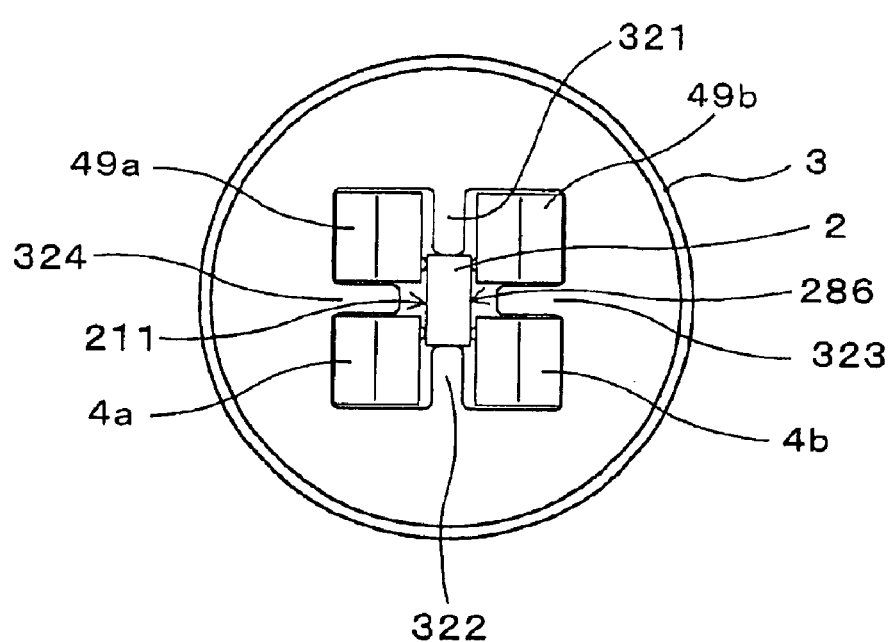

FIG. 10 is a cross-sectional view in a larger scale showing a mechanical relationship between a resilient terminal and a ceramic element disposed in an insulator of a gas sensor according to the first embodiment.

FIG. 11A is a side view of a resilient terminal according to the first embodiment.

FIG. 11B is a top view of a resilient terminal according to the first embodiment.

FIG. 12A is a cross-sectional view showing a mechanical relationship among a terminal electrode, a contact slidable area and a conductive through hole according to the second embodiment.

FIG. 12B is a top view showing a mechanical relationship among a terminal electrode, a contact slidable area and a conductive through hole according to the second embodiment.

FIG. 13 is a top view showing a mechanical relationship among a terminal electrode having a width narrower than the width of a ceramic element, a contact slidable area and a conductive through hole according to the second embodiment.

Figure 14:
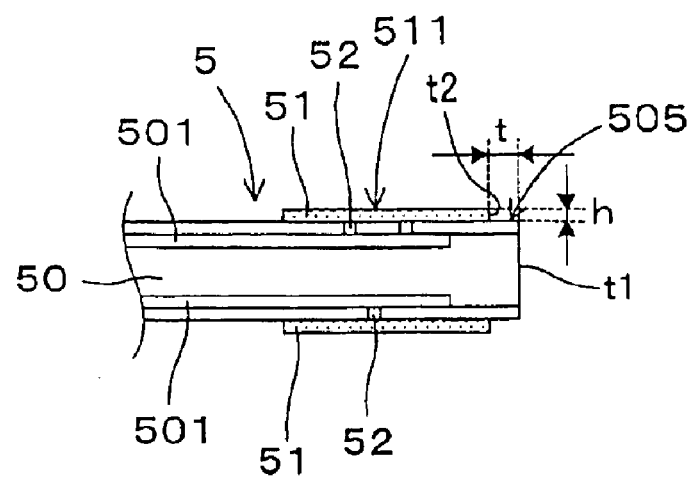

FIG. 14 is a cross-sectional view showing a ceramic element having a terminal electrode disposed inside an end of the ceramic element according to the second embodiment.

Figure 15:
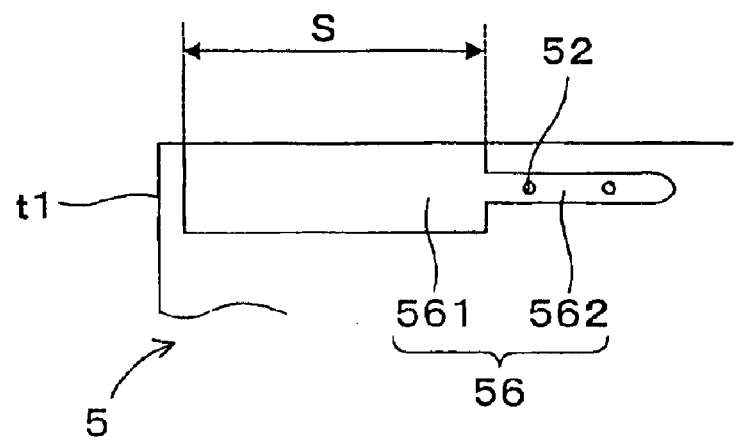

FIG. 15 is a top view showing a mechanical relationship between a terminal electrode having a broader part and a narrower part, and a conductive through hole according to the second embodiment.

Figure 16:
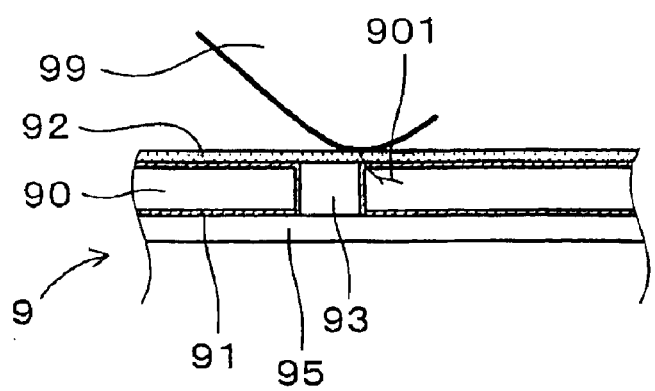

FIG. 16 is a cross-sectional view showing a resilient terminal and a terminal electrode in contact with each other and a crack known in a background art.

Figure 17:
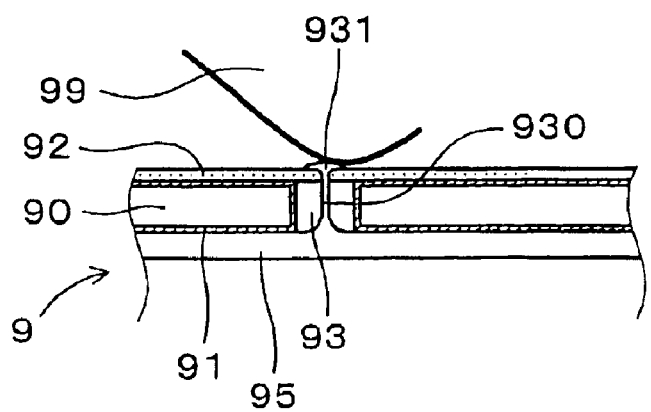

FIG. 17 is a cross-sectional view showing a resilient terminal and a terminal electrode being in contact with each other, and a conductive deterioration, known in a background art.

DESCRIPTION OF THE PREFERRED EMBODIMENTS

Preferred embodiments of the present invention will be described below referring to the drawings.

First Embodiment

As shown in FIGS. 1–11, the contact slidable structure formed between the ceramic element 2 and the resilient terminals 4a,4b,49a and 49b includes the ceramic body 20, the inner leads 282 and 233 build in the ceramic body 20, the terminal electrodes 283 and 236 formed on an upper surface of the ceramic body 20, and the conductive through holes 280 and 234 extending through the inner leads 282 and 233 and the terminal electrodes 283 and 236, respectively, to form an electrical connection therebetween, in which the resilient terminals 4a,4b,49a and 49b are placed to be slidable on the upper surface 2830 and 2360 of the terminal electrodes 283 and 236, respectively. The conductive through holes 280 and 234 are not formed within the contact slidable areas H1 and H2 where the resilient terminals 4a,4b,49a and 49b are slidable on the terminal electrodes 283 and 236, respectively.

Figure 6:
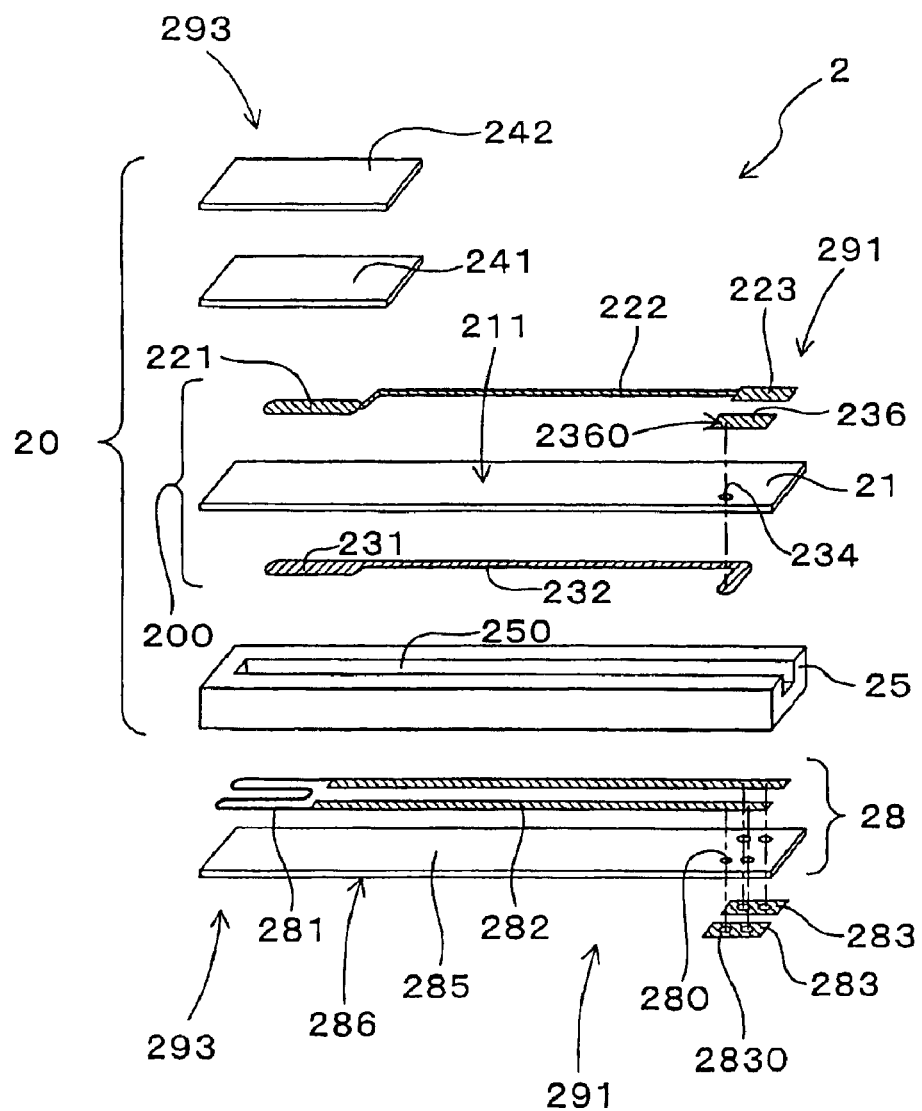
FIG. 6 is a development elevation showing a ceramic element according to the first embodiment.

As shown in FIG. 6, the ceramic element 2 works as a gas sensing element which has the single electrochemical cell 200 for measuring concentration of the predetermined component contained in a measurement gas. The resilient terminals 4a,4b,49a and 49b of the ceramic element 2 are used for feeding electric power to the ceramic element 2 or bringing out an output from the ceramic element 2.

As ways of forming the contact slidable structure between the resilient terminals 4a,4b,49a and 49b and the terminal electrodes 236 and 283, respectively, according to the invention, the following three ways are available, i.e. the first way is to allow the resilient terminals 4a,4b,49a and 49b to move to the sensing element 2, the second way is to allow the ceramic element 2 to move to the resilient terminals 4a,4b,49a and 49b, as described in the first embodiment, and the third way is to allow both the resilient terminals 4a,4b, 49a and 49b and the ceramic element 2 to move. The present invention is applicable to any of the ways of the contact slidable structure.

The contact slidable area is defined between a contact of the resilient terminal 59 coming into contact with the ceramic element 2 when a first holder sustaining the ceramic element 2 is jointed with a second holder accommodating the resilient terminals 4a,4b,49a and 49b and a contact of the resilient terminal 59 in contact with the ceramic element 5 when the joining of the ceramic element 2 and the resilient terminals 4a,4b,49a and 49b is completed. Specifically, the contact slidable area is as clearly shown in FIG. 12, defined between a1 and a2.

The resilient terminal 59 has a width identical with or more than the width of the ceramic element 5 in a lateral direction which is orthogonal to a longitudinal centerline thereof. Therefore, the contact slidable area is extended entirely in the lateral direction of the ceramic element 5, so that conductive through hole 52 is formed in the left side of the straight line a2 shown in FIG. 12.

The first embodiment of the present invention will be described below in more detail. The ceramic element 2, as already described, works as the gas sensing element. The ceramic element 2 is built in a gas sensor installed in an exhaust system of an automotive engine to measure the concentration of oxygen contained in the exhaust gases used to control combustion of the engine or to monitor a deterioration of a catalyst installed in the automotive exhaust system. For instance, EPO 987 546 A2 and U.S. Pat. No. 6,447,887, assigned to the same assignee as that of this application teaches a structure and control of an operation of a gas sensor including this type of gas sensing element in detail, disclosure of which is incorporated herein by reference.

Figure 5:
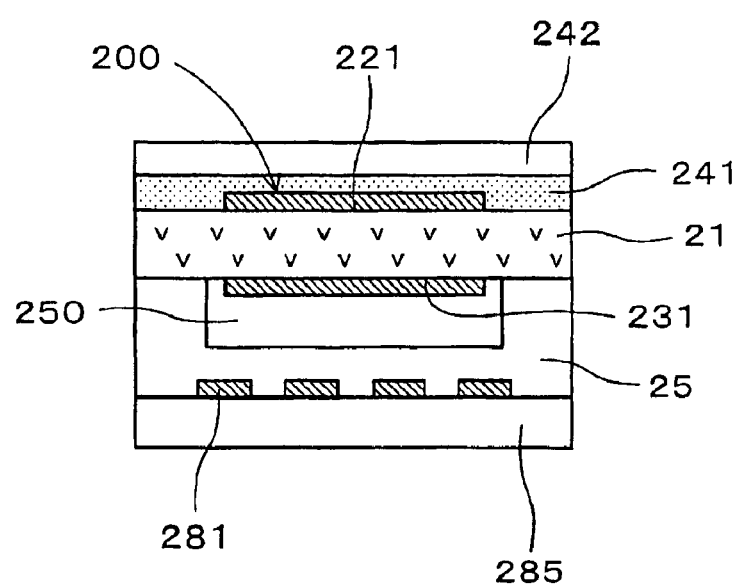
FIG. 5 is a cross-sectional view showing a cross-sectional surface in a laminating direction of a ceramic element according to the first embodiment.

The sensor element 2, as shown in FIG. 5, is made up of the solid electrolytic substrate 21, the diffusion resistant layer 241, the protecting film 242, the spacer 25 and the heater substrate 285 which are laminated vertically as viewed in FIGS. 5 and 6. The sensor element 2 is surrounded by a protective layer (not shown). The solid electrolytic substrate 21 is made of a rectangular partially-stabilized zirconia sheet and has the measurement gas side electrode 221 and the reference electrode 16 affixed to opposed surfaces thereof. The diffusion resistant layer 241 is made of a porous sheet which permits exhaust gasses to flow onto the measurement gas side electrode 221. The protecting film 242 is made of a dense sheet which inhibits the exhaust gasses from passing therethough. The diffusion resistant layer 241 and the protecting film 242 are each formed using a sheet made of ceramic such as alumina, spinel, or zirconia and have average porosities, or gas permeability different from each other.

The spacer 25 is made of a high-temperature conductive material such as ceramic and has formed therein an atmospheric chamber 250 to which the reference electrode 231 is exposed. The spacer 25 has a heating element 281 embedded therein. The heating element 281 is made of heating wire which is supplied with power from a storage battery installed in the vehicle to produce heat the whole of the ceramic element 2 up to a desired activatable temperature.

The exhaust gasses flowing within an exhaust pipe of the engine to which the ceramic element 2 is exposed enter and pass through the side of the diffusion resistant layer 241 and reaches the measurement gas side electrode 221.

As shown in FIGS. 1–6, the electrochemical cell 200 is formed on the top 293 of the solid electrolytic substrate 21.

The electrochemical cell 200, as shown in FIGS. 3–6, is made up of the solid electrolytic substrate 21, the measurement gas side electrode 221 exposed to the measurement gas present outside the ceramic element 2 through the diffusion resistant layer 241, and the reference electrode 231 exposed to the atmospheric chamber 250 formed in the ceramic element 2.

Figure 3:
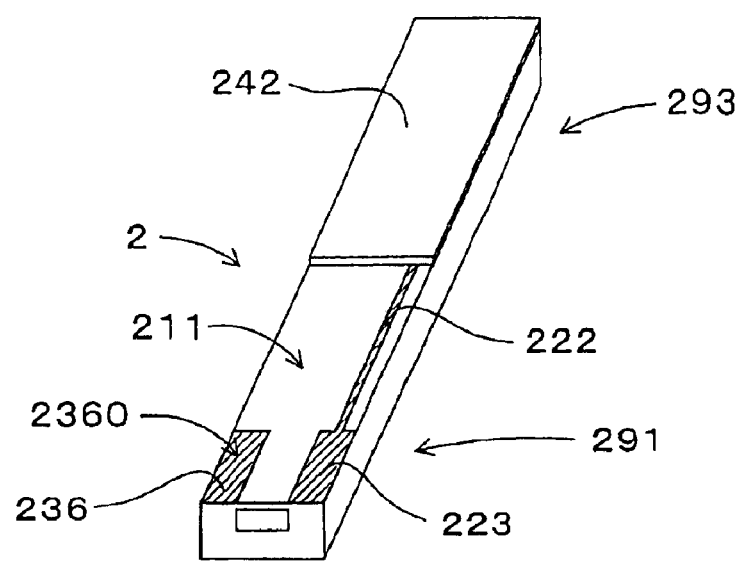
FIG. 3 is an oblique perspective view showing an outer surface (a solid electrolyte substrate side) of a ceramic body of a gas sensing element according to the first embodiment.

As shown in FIGS. 3 and 5, the diffusion resistant layer 241 is covered with a dense and gas impermeable protecting film 242.

As shown in FIGS. 3 and 6, the measurement gas side electrode 221 is electrically connected to the terminal electrode 223 through the outer lead 222. The reference electrode 231 is electrically connected to the terminal electrode 236 through the conductive through hole 234 formed between the inner lead 232 and the solid electrolytic substrate 21.

As shown in FIG. 3, the outer lead 222 and terminal electrodes 223 and 236 are formed on the outer surface 211 of the solid electrolytic substrate 21.

Figure 4:
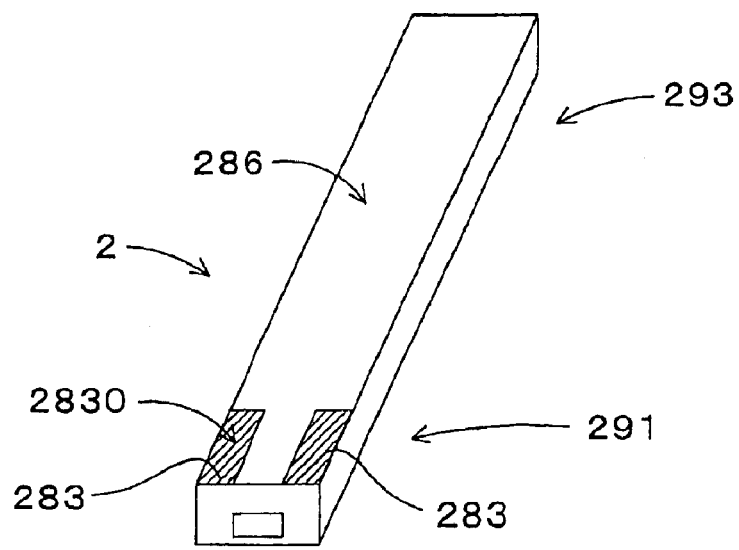
FIG. 4 is an oblique perspective view showing an outer surface (a heater substrate side) of a ceramic body of a gas sensing element according to the first embodiment.

As shown in FIG. 6, the heater 28 is affixed to the ceramic body 20 of the ceramic element 2. As shown in FIGS. 4 and 6, the heater 28 is made up of the heater substrate 285, the heating element 281, the inner lead 282, a pair of the conductive through holes 280 penetrating through the heater substrate 285, and the terminal electrode 283 formed on the outer surface 286 of the ceramic element 2.

The heating element 281 generates heat by electric power. The electric power is fed to the heating element 281 through the inner lead 282, a pair of the conductive through holes 280, and the terminal electrode 283.

Figure 2:
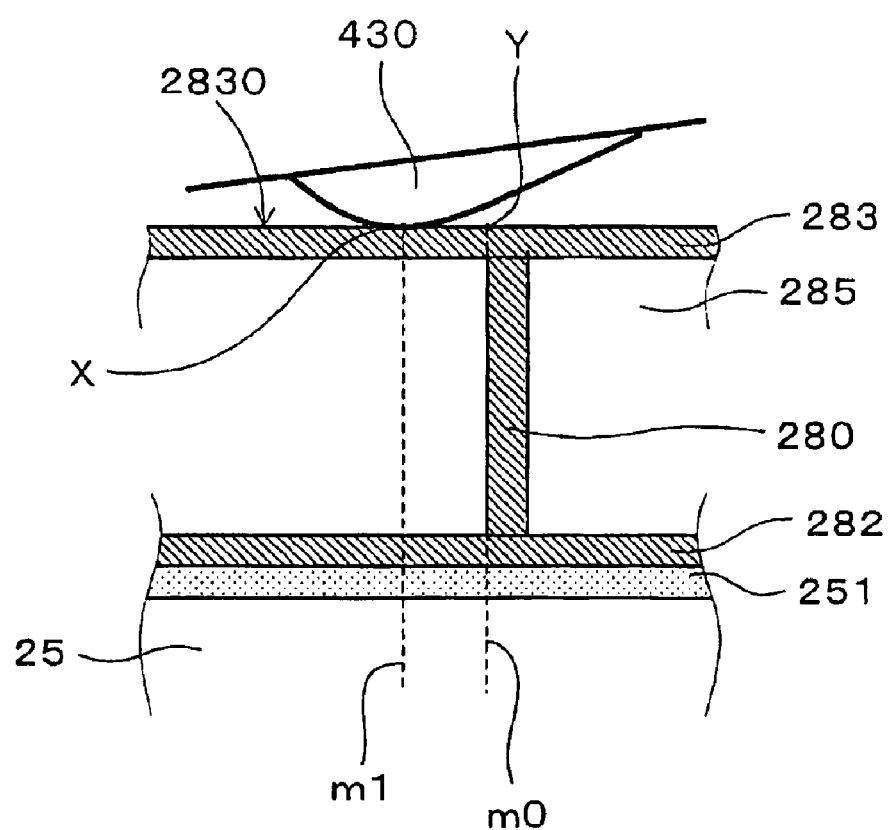
FIG. 2 is a cross-sectional view in a larger scale showing a contact slidable structure formed between a gas sensing element and a resilient terminal according to the first embodiment.

As shown in FIG. 2, the thin insulating layer 251 is formed between the heater substrate 285 and the spacer 25.

In FIGS. 1–6, numerals 2360 and 2830 represent outer surfaces of terminal electrodes 236 and 283, respectively.

The contact slidable structure formed between the ceramic element 2 and the resilient terminals 4a,4b,49a and 49b will be described in detail.

Figure 1:
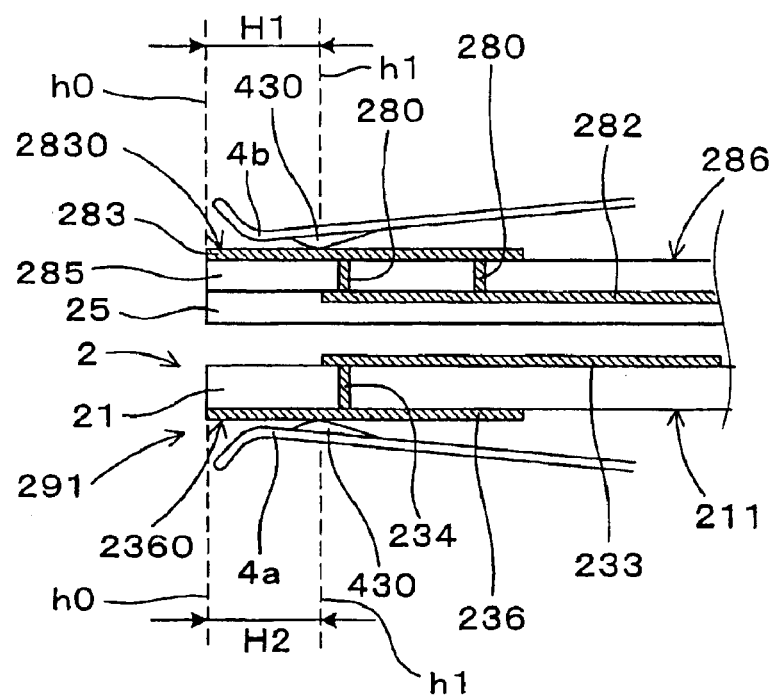
FIG. 1 is a cross-sectional view showing a contact slidable structure formed between a gas sensing element and a resilient terminal according to the first embodiment.

As shown in FIGS. 1 and 2, the projection 430 of the resilient terminal 4a (Although a projection having a shape identical with that of the projection 430 is formed on each of 4b,49a and 49b, we will refer to 4a only, hereinafter.) is in contact with the terminal electrode 283 (Although the projection having the shape identical with that of the projection 430 comes into contact with the terminal the electrode 236, we will refer to the terminal electrode 283 only, hereinafter.) to form an electrical connection at the position of a contact between the resilient terminal and the terminal electrode.

The position of the contact is indicated by the sign X in FIG. 2. Hereinafter, a normal line extending from the end indicated by the sign X on the outer surface 2830 of the terminal electrode 283 to inside the ceramic element 2 will be referred to as m1.

Another normal line extending from the end indicated by the sign Y, which is the nearest to the end indicated by the sign X of the conductive through hole 280 electrically connected to the terminal electrode 283, to inside the ceramic element 2 will be referred to as m0.

Thus, the spacing between the normal line m1 and the normal line m0 is the shortest distance between the end of the contact slidable area H2 of the resilient terminal 4a and the conductive through hole 280 which is electrically connected to the terminal electrode 283. In the ceramic element 2 of the first embodiment, the spacing is 0.5 mm.

The spacing between the conductive through hole 280 formed on the terminal electrode 283 and an end of the sliding is preferably at least 0.5 mm.

Because a portion of the heater substrate 25 in the vicinity of the conductive through hole is fragile, by means of constructing so as to terminate the sliding of the resilient terminal 4a at a location apart from the conductive through hole 280, both occurrence of cracks running from the edge of the conductive through hole 280 to the ceramic body 20 due to a pressure applied by the resilient terminal 4a, and formation of insulating coating on an upper surface of the terminal electrode 283 is prohibited.

In case that the above distance between the conductive through hole 280 and the endpoint of the sliding is less than 0.5 mm, the effect of protecting the ceramic body 20 in the vicinity of the conductive through hole 280 from breaking may be insufficient.

The gas sensor 1 having the ceramic element 2 of the first embodiment built in will be described. As shown in FIG. 8, the gas sensor 1 includes the housing 10, the atmosphere-side cover 121 installed on the base side (an upper end) 101 of the housing 10, the measurement-gas-side covers 141 and 142 disposed on the front end (the lower end) 102. The measurement gas-side covers 141 and 142 constitute a cover assembly having a double-wall structure.

The ceramic element 2 is retained within the housing 10 through the lower insulator 13. As shown in FIGS. 1–6, the base side 291 of the ceramic element 2 having the terminal electrodes 283 and 235 disposed thereon is held in the insulator 3 fixed in the atmosphere-side cover 121, while the top side 293 having the measurement gas side electrode 221 thereon is disposed in the measurement-gas-side cover 142.

The atmosphere-side cover 121 is welded to the base side 101 of the housing 10. The atmosphere-side cover 122 is fixed to the upper portion of the atmosphere-side cover 121 by crimping. The water repellent filter 125 is disposed between the atmosphere-side covers 121 and 122. The ceramic element 2 is inserted into the tubular lower insulator 13 fixed in the housing 10, and fixed there. A gap between the ceramic element 2 and the lower insulator 13 is sealed with the glass sealant 131.

The insulator 3 is disposed on an upper portion, i.e. a base side of the lower insulator 13 fixed in the atmosphere-side cover 121.

The rubber bush 129 is disposed on an upper portion, i.e. a base side of the insulator 3.

The rubber bush 129 has four terminal holes, into which four leads including the leads 161 and 163 (only two are shown for the brevity of illustration) are inserted, respectively. The four leads including the leads 161 and 163 are connected to the four resilient terminals 4a,4b,49a and 49b, through the metal members 151 and 153, respectively.

In the gas sensor 1, the insulator 3 and the atmosphere-side covers 121 and 122 are contained in the first holder. The lower insulator 13, the housing 10, and the measurement gas-side covers 141 and 142 are contained in the second holder.

As shown in FIGS. 9A,9B,and 10, the insulator 3 has four terminal holes each of which has a substantially square section. On an around of a center line of the insulator 3, each of the four terminal holes is connected to the element hole 320. A portion of the inner wall of the insulator 3 between adjacent two of the terminal holes, projects toward the center line to form the ribs 321, 322, 323 and 324.

As shown in FIGS. 9A, 9B and 10, the resilient terminals 4a,4b,49a and 49b are installed in the terminal holes, sandwiching the ribs 321, 322, 323 and 324 respectively.

As shown in FIGS. 11A and 11B, the resilient terminal 4a has the connecting portion 41 and the resilient contact portion 45. The connecting portion 41 and the resilient contact portion 45 are united through the shoulder 40 bent at right angles.

The resilient contact portion 45 has the back surface 42 facing terminal holes 311–314, the element contact surface 43 facing the ceramic element 2, and the portion 44 folded toward the back surface 42.

The projection 430 is formed on the element contact surface 43. The slope of the projection 430 is formed so that one side of the projection 430 for receiving the ceramic element 2, i.e. the angle between the sloped surface 431 and a flat surface of the resilient terminal 4a in the vicinity of the projection 430 is looser than the angle between the sloped surface 432 and a flat surface of the resilient terminal 4b in the vicinity of the projection 430, on the opposite side.

The center line 410 of the connecting portion 41 of the resilient terminal 4a and the center line 450 of the resilient contact portion 45 are out of alignment. As apparent from FIG. 11B, the center line 450 is shifted rightward as viewed in FIG. 11B. The projection 430 is shifted leftward of the center line 450 in FIG. 11B.

The shape of the resilient terminal 4a and the resilient terminal 49a are in a mirror image to each other.

Although detailed drawings of the resilient terminal 49a are abbreviated, the center line 450 is shifted leftward of the center line 410. The projection 430 is shifted rightward the center line 450. Both the wordings "rightward" and "leftward" indicate the direction in FIG. 11B The resilient terminal 4b is identical in shape with the resilient terminal 4a. The resilient terminal 49b is identical in shape with the resilient terminal 49a.

FIG. 10 illustrates the ceramic element 2 inserted into the element hole 320. The resilient terminals 4a and 49a face the outer surface 211 of the ceramic element 2. Each of the terminal electrodes 223 and 236 is disposed on the outer surface 211. The terminal electrodes 223 and 236 are electrically connected to the electrodes 221 and 231, respectively, which constitute the electrochemical cell 200 of the ceramic element 2. The resilient terminal 4a is slidable on the terminal electrode 236. The resilient terminal 49a is slidable on the terminal electrode 223.

The resilient terminals 4b and 49b face the outer surface 286 of the ceramic element 2. A pair of the terminal electrodes 283 for feeding electrical power to the heating element 281 of the ceramic element 2 are formed on the outer surface 286. The resilient terminals 4b and 49b are slidable on the terminal electrodes 283, respectively.

The ceramic element 2 is so disposed in the element hole 320, that each of the resilient terminals 4a,4b,49a and 49b is slidable on one of the terminal electrodes 223, 236 and 283 of the ceramic element 2.

The base side 291 of the ceramic element 2 is disposed within the element hole 320 formed in the insulator 3, and is allowed to slide to the resilient terminals 4a,4b,49a and 49b, thus, the resilient terminals 4a,4b,49a and 49b are slidable on the terminal electrodes 223,236 and 283, respectively.

As shown in FIG. 7A, the base side 291 of the ceramic element 2 comes into contact with the element contact surface 43 of the resilient terminal 4a when the ceramic element 2 is pushed in a direction indicated by the arrow K1. The surface 2360 of the terminal electrode 236 formed on the ceramic element 2 slide in a direction from the element contact surface 43 to the projection 430, as shown in FIG. 7B, then the ceramic element 2 is stopped at the moment the projection 430 reaches to a predetermined location.

As shown in FIGS. 1 and 7, the contact slidable area H2 is defined as a space between the end position h0 located on the base side 291 of the ceramic element 2 where the ceramic element 2 first comes into contact with the resilient terminal 4a and the position h1 where the projection 430 comes into contact with the terminal electrode 283.

Upon sliding, the resilient terminal 4a is deformed along the arrow K2, as the ceramic element 2 moves in the direction indicated by the arrow K1.

When the contact slidable structure is formed, the position h1 may be selected so that the conductive through hole 234 being electrically connected to the terminal electrode 236 is not encompassed within the contact slidable area H2.

Similarly, the contact slidable areas H1 are determined with respect to the resilient terminals 4b and 49b.

Because the terminal electrode 223 is not connected electrically to an inner lead through the conductive through hole 280, an area on which the resilient terminal 49a slides is not limited.

Advantages of the first embodiment will be described. In the ceramic element 2, because the conductive through holes 280 and 234 are not present within the contact slidable areas H1 and H2, respectively, sliding pressure generated when the resilient terminals 4a,4b and 49b slide over the terminal electrode while being in contact with the terminal electrode, is not applied to the conductive through holes 280 and 234.

Therefore, occurrence of cracks running from the edge of conductive through holes 280 and 234 to the ceramic body 20 due to the sliding pressure, and formation of insulating coating on the outer surfaces 2360 and 2830 of the terminal electrodes 236 and 283 by insulating material exuded from inside of the ceramic body are not likely to arise.

As described above, the contact slidable structure formed between the ceramic element and the resilient terminal provides a high electrical conductivity between the resilient terminal 4a and the terminal electrode 283.

Furthermore, the contact slidable structure may be used with a gas sensing element.

The above ceramic element 2 is the gas sensing element having at least one electrochemical cell 200 for measuring concentration of a predetermined component contained in the measurement gas. The resilient terminal 4a of the ceramic element 2 is used for feeding electrical power to the gas sensing element or bringing out the output from the gas sensing element.

The electrical connection between the resilient terminal 4a and the terminal electrode 236 is assured, and hence reliability of the gas sensor is enhanced.

In addition, the gas sensing element for measuring the concentration of oxygen gas, NOx, CO, HC, or the predetermined component may be exemplified as the gas sensing element.

Furthermore, the gas sensing element having a plurality of electrochemical cells and a plurality of contact slidable structures according to the present invention may be exemplified as the gas sensing element.

In the following embodiments, several ceramic elements having various relationships among the contact slidable area, the terminal electrode and the conductive through hole will be described.

Second Embodiment

In the second embodiment, as shown in FIGS. 12A and 12B, a contact slidable structure is formed between the ceramic element 5 and the resilient terminal 59a.

The ceramic element 5 includes the ceramic body 50, the inner lead 501, and the conductive through hole 52. The resilient terminal 59a has a width identical with or more than that of the ceramic element 5.

As shown in FIG. 12B, the contact slidable area H3 extends over the ceramic element 5 in a lateral direction thereof, indicated by the sign W. As shown in FIG. 12B, the contact slidable area H3 is defined as a square area by the dotted lines a1 and a2, i.e. the surfaces of the terminal electrode 51 and the ceramic body 50 between the dotted line a1 on which the resilient terminal 59 comes into contact with the terminal electrode 51 and the dotted line 2 on which the resilient terminal 59 stops, upon joining the ceramic element 5 with the resilient terminal 59. Thus, as shown in FIGS. 12A and 12B, the conductive through hole 52 is formed leftward of the dotted line a2.

Furthermore, the dotted line a3 represents an end of the conductive through hole 52 which is the nearest to the dotted line a2. The distance between the dotted lines a2 and a3 is the shortest between the conductive through hole 52 and the contact slidable area H3.

The rest of the arrangement of the second embodiment is substantially identical with that of the first embodiment. Hence, the second embodiment brings substantially the same functions and effects.

Third Embodiment

The third embodiment of the invention will be described.

In this embodiment, as shown in FIG. 13, the width of the resilient terminal (not shown) is narrower than that of the ceramic element 55. The width of the contact slidable area is equivalent to the width of the resilient terminal (not shown), and the contact slidable area is indicated by sign B surrounded by a dotted line in FIG. 13.

The contact slidable area B is selected, so that the conductive through hole 52 is out of alignment to the contact slidable area B in a lateral direction of the ceramic element 55, or leftward of the contact slidable area B in FIG. 13.

In other words, the conductive through hole 52 may be formed leftwards or outside the contact slidable area B in the lateral direction of the ceramic element 55.

The rest of the arrangement of the third embodiment is substantially identical with that of the first embodiment. Hence, the third embodiment brings substantially the same functions and effects.

Fourth Embodiment

In the fourth embodiment, as shown in FIG. 14, the terminal electrode 51 is disposed on the ceramic element 5, such that the end t2 of the terminal electrode 51 is shifted inward the end t1 of the ceramic body 50, in a direction the ceramic element 5 moves to the resilient terminal upon joining the resilient terminal and the terminal electrode 51.

In case that an end of the terminal electrode 51 is named as the end t2, which is a beginning point of the contact slidable structure, the shortest distance between the end t1 and the end t2 in the direction of the contact slidable structure is preferably not less than 0.2 mm.

In case that the shortest distance is less than 0.2 mm, because a large force is applied to the end t2 of the terminal electrode 51 when the resilient terminal comes into contact with the terminal electrode 51, the terminal electrode 51 is likely to be peeled off.

As shown in FIG. 14, a step is formed between the outer surface 511 and the outer surface 505 at the end t2 of the terminal electrode 51. The step has a height equivalent to the thickness h of the terminal electrode 51 measured from the outer surface 505 of the ceramic body 50 at the end t2. The height of the step is 7 $\mu$m.

Furthermore, the terminal electrode 51 preferably has a thickness of 3–50 $\mu$m, measured from the upper surface of the ceramic body 50 on the end t2.

In case that the thickness of the terminal electrode 51 is less than 3 $\mu$m, which is not enough to withstand the force to be applied by the resilient terminal when the resilient terminal slides over the terminal electrode 51, hence the terminal electrode 51 is likely to be peeled off.

In case that the thickness of the terminal electrode 51 is more than 50 $\mu$m, because a large force is applied to the terminal electrode 51 by the resilient terminal when the resilient terminal comes into contact with the terminal electrode 51, the terminal electrode 51 is likely to be peeled off.

According to the above structure, the resilient terminal is placed slidable on the upper surface 511 of the ceramic element 5 in the direction from the end t1 to the terminal electrode 51 to form a contact slidable structure between the resilient terminal and the terminal electrode 51. When the ceramic element 5 is inserted into the hole, the resilient terminal first comes into contact with the outer surface 505 of the ceramic element 5, which has no terminal electrode 51 thereon in the vicinity of the end t1, and then the resilient terminal runs on the step formed between the outer surface 511 and the outer surface 505 at the end t2 of the terminal electrode 51, and slides to a predetermined position.

When the resilient terminal runs onto the outer surface 511 of the terminal electrode 51 from the outer surface 505 of the ceramic body 50 to form the contact slidable structure between the resilient terminal and the terminal electrode 51, the terminal electrode 51 is prevented from being exposed to a large force, thus, the peeling of the terminal electrode 51 is avoided.

In particular, a large force is prevented from applying to the end t2 of the terminal electrode 51, as a result, peeling of the terminal electrode 51 is avoided.

Moreover, because the end t2 of the terminal electrode 51 is apart by the distance t from the end t1 of the ceramic body 50, and the thickness h at the end t2 has the above dimension, the peeling of the terminal electrode 51 is avoided.

The rest of the arrangement of the fourth embodiment is substantially identical with that of the first embodiment. Hence, the fourth embodiment brings substantially the same functions and effects.

Fifth Embodiment

In the fifth embodiment, as shown in FIG. 15, the terminal electrode 56 on the ceramic element 5 is made of two parts, i.e. one is the broader part 561, and another is the narrower part 562.

The terminal electrode 56 is disposed on the ceramic element 5 so that the broader part 561 and the narrower part 562 are arranged along a direction the resilient terminal moves upon joining the resilient terminal and the terminal electrode. The broader part 561 is disposed close to the end t1 of the ceramic element 5, and the narrower part 52 is disposed on an opposite side of the end t1.

The conductive through hole 52 is formed on the narrower part 562, the area indicated by sign S on the broader part 561 in FIG. 15 is the contact slidable area.

Because the width of the terminal electrode 56 is extended to form a broader part 561, an area the resilient terminal comes into contact with the terminal electrode 56 is enlarged, thus, an electrical connection between the resilient terminal and the terminal electrode 56 is ensured.

In addition, because the width of the terminal electrode 56 is narrowed to form the narrower part 562, the amount of material for forming the terminal electrode 56 is reduced to save cost thereof.

The rest of the arrangement of the fifth embodiment is substantially identical with that of the first embodiment. Hence, the fifth embodiment brings substantially the same functions and effects.

What is claimed is:

1. A contact slidable structure comprising:
   an element having a body, an inner lead formed in the body, a terminal electrode formed on an outer surface of the body, and a conductive through hole penetrating the body between the inner lead and the terminal electrode to form an electrical connection therebetween; and
   a resilient terminal slidably placed on an outer surface of the terminal electrode to form a contact with the terminal electrode,
   wherein the conductive through hole is formed outside a contact slidable area on which the contact slides when the element is connected to the resilient terminal.

2. A contact slidable structure as set forth in claim 1, wherein the conductive through hole is apart by at least 0.5 mm from the contact slidable area.

3. A contact slidable structure as set forth in claim 1, wherein the resilient terminal is forced to press the terminal electrode to form the contact.

4. A contact slidable structure as set forth in claim 3, wherein an end t2 of the terminal electrode is apart by at least 0.2 mm from an end t1 of the element.

5. A contact slidable structure as set forth in claim 4, wherein the terminal electrode has a thickness of 3–50 µm at the end t2.

6. A contact slidable structure as set forth in claim 1, wherein the element is a gas sensing element having an electrochemical cell for measuring concentration of a predetermined component contained in a measurement gas.

7. An electrically connecting mechanism comprising:
   a first holder designed to hold an element which has a body and an electric circuit, the electric circuit including a first terminal formed on an outer surface of the body, an inner conductor disposed within the body, and a conductive through hole extending through the body to establish an electrical connection between the first terminal and the inner conductor; and
   a second holder which holds a second terminal, said second holder designed to establish a mechanical joint to said first holder and allow the element to slide on the second terminal and make an electrical contact of the first terminal with the second terminal upon establishment of the mechanical joint to said first holder, the second terminal being elastically deformable to apply a physical pressure to the first terminal of the element through the electrical contact, orientation of the physical pressure being out of alignment with the conductive through hole of the element.

8. An electrically connecting mechanism as set forth in claim 7, wherein the second holder has a hole in which the element is accommodated.

9. An electrically connecting mechanism as set forth in claim 7, wherein the conductive conductive through hole is out of alignment with respect to an area where the physical pressure acts upon establishment of the mechanical joint.

10. An electrically connecting mechanism as set forth in claim 7, wherein the second terminal has a shape deformable in a direction departing from the upper surface of the element, along a normal line thereof.

11. An electrically connecting mechanism as set forth in claim 7, wherein the second terminal is made up of a pair of terminal elements provided in the hole so that the element is clipped between the pair of terminal elements.

12. A gas sensor comprising:
   a sensing element having a length and an electrical circuit sensing density of a predetermined component contained a measurement gas,
   a first holder holding a first end and a portion of a side of the sensing element while exserting a second end and a portion of a side of the sensing element,
   a second holder having a cavity accommodating the second end and the portion of the side of the sensing element,
   an inner lead embedded in the sensing element, electrically connected to the electrical circuit,
   an outer lead disposed on an outer surface of the sensing element,
   a conductive through hole formed at the sensing element, electrically connecting the inner lead with the outer lead,
   a resilient terminal affixed to an inner wall of the cavity, slidably placed on the outer lead,
   a lead assembled in the second holder, electrically connected to the resilient terminal,
   wherein the conductive through hole is formed outside an area on which pressure from the resilient terminal acts.

13. A gas sensor as set forth in claim 12, wherein the sensing element has an embedded atmospheric chamber admitting air thereinto and a solid electrolytic substrate exposed to the atmospheric chamber, admitting the predetermined component thereinto, a solid electrolytic substrate exposed to the atmospheric chamber and a diffusion resistant layer laminated on the solid electrolytic substrate, admitting the predetermined component thereinto, and wherein the electrical circuit comprises a reference electrode affixed to a surface of the solid electrolytic substrate, exposed to the atmospheric chamber and a measurement gas side electrode affixed to the opposite surface of the solid electrolytic substrate.

14. A gas sensor as set forth in claim 12, wherein the conductive through hole is provided inside the area in a longitudinal direction of the sensing element.

15. A gas sensor as set forth in claim 12, wherein the conductive through hole is provided outside the area in a lateral direction of the sensing element.

16. A gas sensor as set forth in claim 12, wherein an end of the terminal electrode is provided inside the second end of the sensing element in a longitudinal direction of the sensing element.

17. A gas sensor as set forth in claim 12, wherein a thickness of the terminal electrode is 3–50 $\mu$m.

18. A gas sensor as set forth in claim 12, wherein the terminal electrode is made up of a broader part locating on an outer surface of the ceramic element in the vicinity of the first end thereof and a narrower part extending toward the second end of the ceramic element.

19. A gas sensor as set forth in claim 18, wherein the conductive through hole is provided on the narrower part.

* * * * *